(12) United States Patent
Thivolet

(10) Patent No.: US 6,342,227 B1
(45) Date of Patent: *Jan. 29, 2002

(54) USE OF IGF-I OR ANALOGUES THEREOF IN THE PREVENTION OF DIABETES

(75) Inventor: Charles Thivolet, Lyons (FR)

(73) Assignee: Chiron Corporation, Emeryville, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,733

(22) PCT Filed: Jun. 22, 1995

(86) PCT No.: PCT/SE95/00776

§ 371 Date: Apr. 7, 1997

§ 102(e) Date: Apr. 7, 1997

(87) PCT Pub. No.: WO96/01124

PCT Pub. Date: Jan. 18, 1996

(30) Foreign Application Priority Data

Jul. 4, 1994 (SE) ............................................. 9402370

(51) Int. Cl.[7] ............................................. A61K 39/00
(52) U.S. Cl. .................................. 424/198.1; 530/303
(58) Field of Search .......................... 424/85.1, 198.1; 530/303

(56) References Cited

U.S. PATENT DOCUMENTS 5,466,670 A * 11/1995 Dunger et al. ................ 514/12
5,583,109 A * 12/1996 Clark et al. .................... 514/12

FOREIGN PATENT DOCUMENTS

| EP | 0123228 | 10/1984 |
| EP | 0308386 | 3/1989 |
| EP | 0331630 | 9/1989 |
| NZ | 218811 | 7/1991 |
| WO | WO9103253 | 3/1991 |
| WO | WO9323071 | 11/1993 |

OTHER PUBLICATIONS

Binz et al., P.N.A.S. USA, vol. 87:3690–3694, May 1990.*
The Protein Folding Problem and Tertiary Structure Prediction, 1994, Merz et al., (ed.) Birkenhauser, Boston, MA. pp. 433 and 492–495, 1994.*
Roget's II, The New Thesaurus, 3rd Ed. Amercian Heritage Dictionaries (ed.) Houghton Mifflin Co. Boston New York, 1995.*
Diabetes, vol. 40, Apr. 1991. Luciano Rossetti et al. *Metabolic Effects of IGF–1 in Diabetic Rats*, p. 444–p. 448.
Trends in endocrinology and metabolism, 1990. E. Rudolf Froesch et al. *Therapeutic Potential of Insulinlike Growth Factor 1*, p. 254.
Cascieri et al. (1989), *J. Biol. Chem.* 264, 2199–2202.
Bayne et al. (1988), *J. Biol. Chem.* 263, 6233–6239.
Oh et al. (1993), *Endo.* 1337–1344.
Cascieri et al. (1988), *Biochemistry* 27, 3229–3233
Cooke et al. (1991), *Biochemistry* 30, 5484–5491.
Maly et al. (1988), *J. Biol. Chem.* 263, 7068–7072.
Sato et al. (1993), *Intl. J. Peptide Res.* 41,433–440.
Zhang et al. (1994), *J. Biol. Chem.* 269, 10609–10613.
Sato et al. (1992), *J. Biochem.* 111,529–536.
Chemical Abstract No. 114: 136379k, 1991.
Schoenle et al, *Diabetologia* (1991) 34: 675–679.
Amiel et al, *The New England Journal of Medicine*, Jul. 24, 1986, 315:4, pp. 215–219.
Guller et al, *The New England Journal of Medicine*, Jul. 16, 1987, 317:3, pp. 137–140.

* cited by examiner

Primary Examiner—Patrick J. Nolan
(74) Attorney, Agent, or Firm—Dinsmore & Shohl LLP

(57) ABSTRACT

IGF-I or an analogue thereof is administered to delay the clinical onset of diabetes, to reduce the occurrence of beta cell destruction in a subject having a high risk of developing diabetes, to provide a regulating effect on spleen T cells in a subject having a high risk of developing diabetes, or to reduce the likelihood of the occurrence of clinical diabetes in a subject having a high risk of developing diabetes.

12 Claims, 3 Drawing Sheets

USE OF IGF-I OR ANALOGUES THEREOF IN THE PREVENTION OF DIABETES

The present invention relates to the use of IGF-I or analogues thereof in the manufacture of a medicament useful in the prevention and delaying the clinical onset of diabetes and having a protective effect against diabetes. The medicament is also useful in preventing beta cell destruction and regulating of T cells.

SUMMARY

Insulin like growth factor-1 (IGF-1) and insulin are structural homologues, and elicit insulin-like and growth-promoting effects. In addition, IGF-1 has important effects on thymocyte replication and function independently of those of insulin. To evaluate the effect of IGF-1 on the autoimmune process of beta cell destruction, permissive recipients were adoptively transferred with T cells from diabetic donors and 10 µg of rhIGF-1 were administered subcutaneously twice daily. The recipients of $7 \times 10^6$ autoreactive T cells were followed for clinical manifestations of diabetes and examined for in situ lesions after three weeks of treatment. We observed that the administration of rhIGF-1 delays the clinical onset of the disease and reduces the final incidence of successful transfers since diabetes was observed in only 6/24 (25%) vs 12/21 (57%) in control mice. These effects were associated with a marked reduction of insulitis. Mice treated with rhIGF-1 had a higher percentage of intact islets (48.6±12% vs 1.6±1.1%, p=0.001) and a lower percentage of infiltrated islets. However, some mice developed diabetes despite rhIGF-1 administration with severely infiltrated islets, indicating thus that committed T cells were still able to invade the islets and cause beta cell destruction. Three weeks after sub-lethal irradiation and T cell inoculation no difference was noticed in the percentages of $CD4^+$ and $CD8^+$ T cells in the spleen of experimental mice. To further elucidate whether rhIGF-1 could influence the homing of committed T cells, we adoptively transferred congenic NOD-N Thy-1,1 mice with T cells from diabetic NOD Thy-1,2 mice and monitored the numbers of $Thy-1,2^+$ T cells present in lymphoid organs after three weeks of treatment. The administration of rhIGF-I was found to reduce significantly the percentage of $Thy-1,2^+$ T cells in the spleen (10.8±1.3% vs 17.2±3.9%, p=0.004) in contrast to the thymus (68.4±7.9% vs 72.87±6.2, p=0,306). The findings that rhIGF-1 has protective effects and may act prior to islet cell invasion opens new perspectives for future experiments and preventive strategies in human type 1 diabetes.

INTRODUCTION

The non-obese diabetes (NOD) mouse is an experimental model of spontaneous diabetes resembling human type 1 (insulin-dependent) diabetes, which results from the progressive islet invasion and beta cell destruction by autoreactive T cells (1,2). This spontaneous diabetes model offers a unique opportunity of studying the autoreactive T cells involved in the process of beta cell destruction and of settling preventive strategies before clinical onset of the disease. The number of committed T cells in the spleens of diabetic animals (3) and the respective contribution of T cell subsets (4) can be evaluated in vivo during adoptive T cell transfer into non diabetic syngeneic animals.

Insulin like growth factor-1 (IGF-1), a 70-amino acid peptide structurally related to insulin, is normally considered to be a metabolic hormone which mediates many effects of growth hormone. Prophylactic insulin treatment of NOD mice during the prediabetic phase (5) as well as insulin treatment of the NOD recipients of autoreactive T cells during adult T cell transfer (6) have been shown to prevent and/or delay the onset of diabetes and to reduce the severity of insulitis. Similar results have been also obtained in BB rats (7,8), which are another animal model of spontaneous autoimmune diabetes. Since insulin is a major antigenic component of the beta cells, it was not clear from these experiments whether insulin protective effects were explained by an antigen-specific unresponsiveness of the immune system, by a direct suppressive effect on T cell function, or by a direct effect on the beta cells.

The present study was undertaken to examine whether rhIGF-1 may have protective effects in the autoimmune diabetes of NOD mice using adoptive T cell transfer experiments.

THE INVENTION

The invention relates to the use of IGF-I or analogues thereof in the manufacture of a medicament useful in the prevention of diabetes and in delaying the clinical onset of diabetes.

IGF-I has also shown to have a protective effect against diabetes, in preventing beta cell destruction in subjects which are at high risk of development of diabetes and in the regulation of T cells in subjects which are at high risk of developing diabetes.

The invention relates to a method for treating patients having the above mentioned problems by administration of IGF-I or analogues thereof.

Possible daily dosages of IGF-I are 20 to 500 µg/kg or preferably 20 to 250 µg/kg or more preferably 100 to 200 µg/kg.

BRIEF DESCRIPTION OF THE DRAWING

The following FIGURES are illustrating the results of the experiments.

MICE AND METHODS

1. Mice

Figure 1:
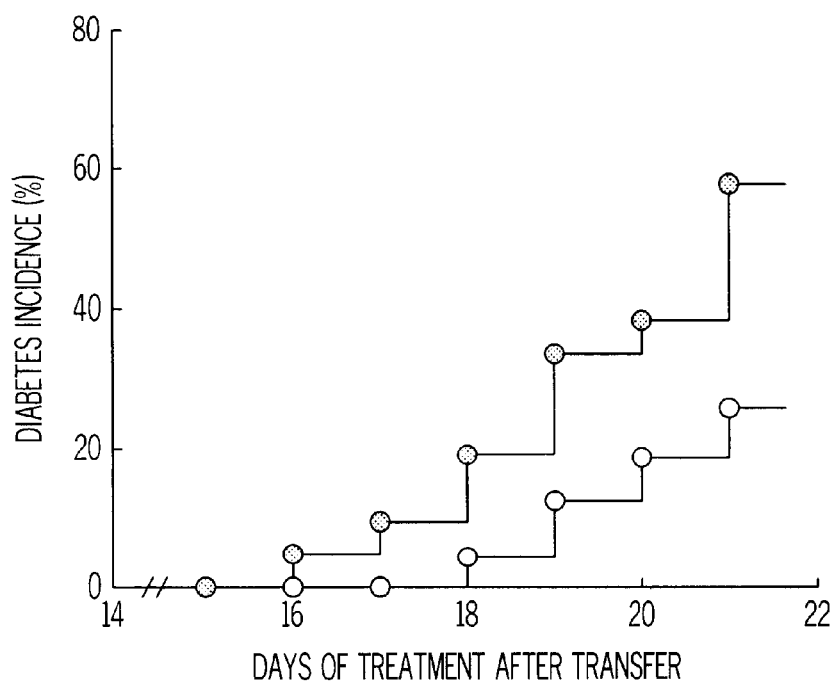
FIG. 1 Cumulative incidence of diabetes in four independent experiments in mice.

NOD mice were bred under standard conditions in our own facilities. The incidence of spontaneous diabetes in our colony reached 80% in females by 30 weeks whereas diabetes occurred in only 20% of males in the same period. Congenic NOD-N Thy-1,1 mice initiated from a cross between NOD/Lt and a diabetes resistant strain NON/Lt were obtained from Ed. Leiter, Bar Harbor Mich. (10). Diagnosis of diabetes was characterized by polydipsia, weight loss, glycosuria (Urine chemstrips, Ames-Bayer, Germany) and persistent hyperglycemia (Blood glucose chemstrips, Lifescan USA). Diabetic NOD females served as donors of autoreactive T cells. Four different experiments of adoptive cell transfer of diabetes were performed using 46 male recipients and 22 diabetic females.

2. Cells

Splenocytes from diabetic mice were isolated in Hanks' balanced salt solution (HBSS) and enriched T cell populations were obtained by filtration through nylon wool columns eluting 20 to 25% of the initial cell preparation. More than 90% of the final cell suspension was from the Thy 1,2+ phenotype during flow cytometry analysis. After numeration and viability evaluation, $7.10^6$ T cells were i.v. injected into 8 to 10 week-old irradiated NOD males (750 rads) according to the method of Wicker et al (3).

3. Protocol of Treatment

Fast-acting insulin stock solution (Actrapid HM, Novo Nordisk Copenhagen, Denmark) was prepared with a 9% NaCl solution at a final concentration of 5 U/ml. Recombinant human IGF-1 (rhIGF-1) was obtained from Dr Anna Skottner (Kabi Pharmacia, Stockholm, Sweden) and aliquoted to a final concentration of 100 μg/ml. The day following adoptive cell transfer, mice were s.c. injected twice daily 100 μl containing either 0.5 U of insulin, 10 μg of rhIGF-1 or saline. Recipient mice received approximately 30 U/kg/day of insulin and 0.6 mg/kg/day of rhIGF-1 over a period of three weeks. The onset of glycosuria was monitored daily starting at day 15.

4. Histologic Procedures

All mice were killed by cervical dislocation. Pancreatic glands were excised and processed for conventional histological studies after fixation in Bouin's alcoholic solution. Five μm sections were stained with haematoxylin-eosin, as described previously (6). The severity of insulitis was scored for at least 25 islets for each specimen, wherein islet cells which had no visible sign of inflammation were scored 0, islets which had lymphocytes at the periphery i.e. peri-insulitis were scored 1, islets which were mildly infiltrated (<40%) were scored 2, islets which were completely infiltrated were scored 3. The percentages of islets of each category were compared between the different groups of mice. The number of beta cells was determined by immunohistochemistry on fixed sections, using an anti-human insulin monoclonal antibody (Novoclone HUI 018, NovoBiolabs, Bagsvaerd Denmark) diluted 1:50 and an anti-human proinsulin monoclonal antibody (Novoclone HPUI). An FITC rabbit anti-mouse IgG (Dako, Burlingame USA) dilution 1:50 was used as a conjugate.

5. T Cell Subset Analysis

After 3 weeks of treatment, spleens from experimental animals were subjected to T cell subset analysis using an anti-Thy1,2 (clone 30H12), anti-L3T4 (clone GK 1,5) and anti-Lyt2 (clone 53–67) rat monoclonal antibodies and a FITC-conjugated anti-rat IgG kappa antibody (MARK-1, Biosys, Compiegne France). To evaluate the influence of rhIGF-1 treatment upon the homing of autoreactive T cells, the percentages of Thy-1,2+ T cells injected into NOD-N Thy-1,1 recipients were determined in lymphoid organs by FACS analysis as well as in islet infiltrates by immunohistochemical procedures on pancreatic sections.

6. mRNA Studies

In order to study the number of mRNA transcripts for insulin in the pancreas of experimental mice, the total RNA content was precipitated in 4M guanidine thiocyanate and then in 7.5M guanidinium hydrochloride (Sigma, St-Louis Mo.) solutions and extracted in chloroform-butanol (100/24, vol/vol). Four different concentrations of ARN ranging from 2.5 to 20 μg were hybridized on nylon membranes with P32-labelled cDNA rat proinsulin probes(obtained from C. Dagorn, Marseille France). Films were analyzed by densitometric scanning after 24 hrs of exposure period.

7. Statistical Analysis

The effects of treatment on diabetes transfer were analyzed using the Wilcoxon test. Scores of insulitis were compared using Student't test for unpaired samples.

RESULTS

Effects of rhIGF-1 Treatment on T Cell Transfer of Diabetes

In order to evaluate the effects of hormonal treatment on the diabetes transfer capacity of autoreactive T cells, we initiated the injection protocol on the day following the adoptive T cell transfer and continued for an overall period of three weeks. The effects of rhIGF-1 on blood glucose levels were determined in a separate experiment. Glucose levels dropped significantly (81.5±0.7 mg/dl) 30 minutes after a single s.c. injection of 10 μg of rhIGF-1, and after 2 hours increased above normal values (181±19.8 mg/dl) before returning to baseline. During the treatment period, the effects of rhIGF-1 on body weight were monitored every two days. rhIGF-1 was able to maintain the body weight of recipient mice, in contrast to saline and/or insulin injections, (Table I). However, these effects were closely dependent on the presence of clinical diabetes.

The occurence of clinical diabetes was determined in rhIGF-1 treated mice and compared with saline and insulin treated groups. Diabetes was detected in only 6 out of 24 (25%) mice treated with rhIGF-1, in contrast to 12/21 (67%) in control mice and 6/14 (42.8%) mice treated with insulin. Insulin like growth factor-1 was associated with a significant reduction in diabetes incidence (p=0.016) as shown in FIG. 1 with a significant delay in the clinical onset of the disease. In addition, insulin-treated mice (p–0.01) also had a significantly lower incidence rate of diabetes than control mice. The treatment of diabetic NOD females with rhIGF-1 twice daily over a period of 7 days prior to transfer, failed to modify the number and degree of activation of the autoreactive T cells contained in the spleens of experimental animals and the diabetes incidence curves were found to be the same after one month.

Histological Studies

Figure 2:
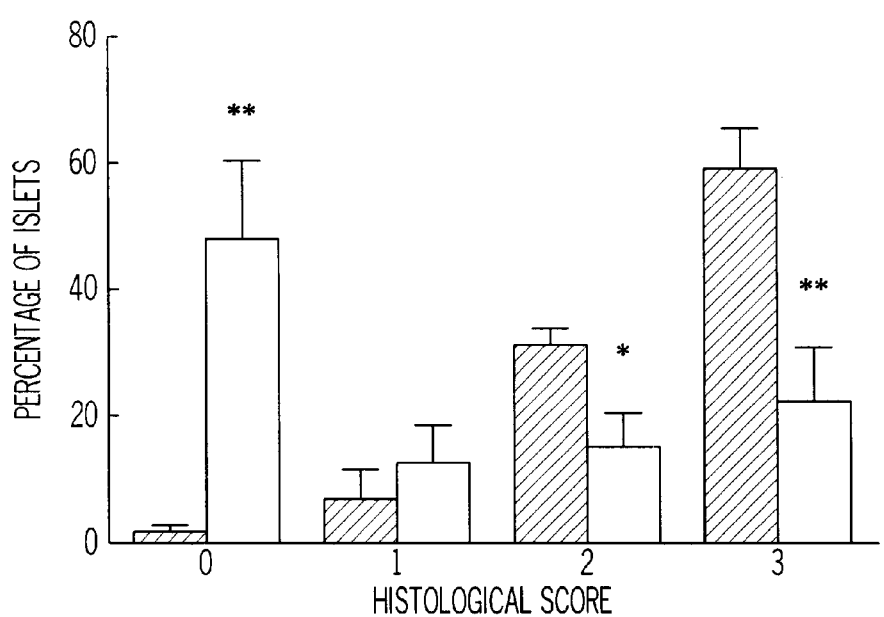
FIG. 2 Severity of insulitis and destructive lesions.

The severity of insulitis was quantified and a comparison was made between the different experimental groups of animals. As shown in FIG. 2, when compared to sham-injected mice, mice that had been treated with rhIGF-1 were found to have a higher percentage of normal (e.g. non infiltrated) islets (48.6±12.1% vs 1.62±1.1%, p=0.001) and a lower percentage of islets with mild (15.8±5.1% vs 31.5±2.8%, p=0.016) or severe insulitis (22.43±8.8% vs 59.82±6.5%, p=0.003). However, no significative difference was found in the percentage of peri-insulitis (7±4.5% vs 13.1±5.8%, p=0.424).

Interestingly, islets from 4/12 mice which received rhIGF-1 were free from lymphocytic infiltration in contrast to 0/11 mice in the control group. Thus, rhIGF-1 reduced both the intensity and the prevalence of insulitis.

Effects of rhIGF-1 on Insulin Synthesis

Although the number of intact beta cells was higher in rhIGF-1 treated animals, no difference was noticed in the intensity of the fluorescent pattern of the remaining beta cell at the end of the treatment period in mice that had been treated with either rhIGF-1 or with saline. In addition, the levels of mRNA transcripts for proinsulin in non diabetic mice during dot blot analysis were comparable in both situations, thus indicating that at the doses used in the present experiments rhIGF-1 does not modulate significantly the rate of insulin synthesis.

Effects of rhIGF-1 on T Cell Homing

Because insulitis is a T cell phenomenon, we suspected that rhIGF-1 might interfere with the kinetics of the migration of committed T cells to the pancreas. Congenic NOD-N Thy-1,1 males were adoptively transferred with T cells from diabetic NOD Thy-1,2 animals. Diabetes occurred in 3/6 mice that had been treated with saline and 0/6 mice that had been treated with rhIGF-1, after 3 weeks of treatment. This apparent protective effect was also associated with a decrease in the severity of islet cell infiltrates, which were composed exclusively by T cells from donor origin with no recruitment of host T cells. More particularly, immunodetection of Thy-1,2$^+$ T cells in the islets of congenic NOD-N Thy-1,1 mice three weeks after adoptive cell transfer of diabetes using 7×10$^6$ T cells from NOD Thy-1,2 diabetic donors illustrates a severe insulitis in a control mouse while illustrating a peri-insulitis in a mouse treated with rhIGF-1. Additionally, when analyzed in individual mice, the number of Thy-1,2$^+$ T cells was found to be significantly lower in the spleen of treated mice with rhIGF-1 in comparison with control mice (Table III and FIGS. 3a, 3b and 3c), although no significant difference was noted within the thymus (FIGS. 4a, 4b and 4c).

DISCUSSION

The adoptive T cell transfer model in the NOD mouse explores in vivo the capacity of autoreactive T cells to cause destructive lesions and ultimately type I diabetes. In the present study, we have demonstrated that rhIGF-1 is able to reduce the capacity of large amounts of committed T cells from invading NOD islets during adoptive T cell transfer. These results reproduce those previously obtained with human insulin (6). However, the present experiments clearly demonstrate that rhIGF-1 is more potent than insulin in preventing diabetes transfer at concentrations 10 times less to those giving comparable metabolic effects in diabetic rats (11). Despite the injection of high numbers of autoreactive T cells, rhIGF-1 was found to delay the time of onset and to reduce the maximal frequency of clinical diabetes. In addition, strong histological evidence indicate that rhIGF-1 prevents massive islet cell invasion and fully protects one third of the treated mice.

There are distinct classes of mechanisms which may be responsible for the prevention of beta cell destruction by IGF-1. First, the effect may be on the beta cells. Specific receptors on the surface of beta cells as well as local production of this growth factor have been identified (12). Recently, an enhanced IGF-1 gene expression has been shown in regenerating rat pancreas after partial pancreatectomy (13,14). However, we were unable to find any difference in the number of insulin and/or proinsulin positive cells within the islets. However, the conservation of insulin-producing beta cells was associated with a marked reduction in islet infiltration, suggesting that the contribution of beta cell regeneration was not essential. Insulin-like growth factor 1 may also on the other hand, be considered as a regulator of insulin release in view of its inhibitory effects at physiological concentrations (15). Although the hypothesis of beta cell rest formulated during early and prolonged insulin therapy (5) might also be evacuated, no difference was noticed in the intensity of insulin staining of the beta cells and in the number of mRNA transcripts for proinsulin.

The observation of pancreatic glands free from insulitis under rhIGF-1 treatment, suggests another mechanism that occurs prior to the late activation process of infiltrating T cells by eliminating or inactivating the functional properties of autoreactive T cells necessary for beta cell destruction. Recombinant hIGF-1 may exert these effects directly on lymphoid cells, since in vitro suppression of T cell response to concanavalin A or allogeneic stimulation can be achieved in a dose dependent manner (16). Many actions of growth-hormone on the immune system may be mediated by IGF-1 which is also produced by peripheral leukocytes (17). Recent observations suggest that activated T lymphocytes possess receptors for IGF-1 (18–20). In addition, several reports indicate that IGF-1 may influence thymic epithelial cell function in vitro (21) and induce thymocyte replication and differentiation in streptozocin induced diabetic rats (22). Mice which receive 4 mg/kg per day of rhIGF-1 were found to have an increased spleen and thymus weight, due to an increase in the number of lymphocytes in these organs, preferentially T cells from the CD4 phenotype (22). We did not observe any difference in the number of T cells in the lymphoid organs and in the relative contribution of T cell subsets within the spleen, probably because of lower doses of rhIGF-1 used in the present study. Moreover, treatment of diabetic females with rhIGF-1 failed to reduce the capacity of spleen cells to transfer the disease, suggesting that the number and degree of activation of autoreactive T cells were not modified.

The effect may be also on the mechanisms of T cell trafficking into the islets during the 10 days period after T cell inoculation that precedes islet cell invasion (23). T cell homing to the pancreas and endothelial-lymphocyte interactions might be regulatory events. Reconstitution of the thymus of irradiated congenic NOD-N Thy-1,1 recipients with Thy-1,2$^+$ T cells was not influenced by rhIGF-1. The significant reduction in the number of T cells from donor origin noticed within the spleen may contribute to the protective effects of IGF-1 during adoptive T cell transfer. A reduction in the number but not in the degree of activation of autoreactive T cells may explain why rhIGF-1 treated mice are not fully protected and why diabetes can still occur.

From the present observations, rhIGF-1 should be considered as an important regulator of autoreactive T cells through autocrine but also endocrine actions, which might have clinical consequences during the prediabetic phase in human type 1 Diabetes.

LEGENDS OF FIGURES

FIG. 1: Cumulative incidence of diabetes in four independent experiments following adoptive T cell transfer in 24 mice injected twice daily with 10$\mu$ rhIGF-1 (open circles) and 21 control mice injected with saline (closed circles).

FIG. 2: Severity of insulitis and destructive lesions of recipient mice according to treatment with saline (dark columns) or rhIGF-1 (open columns). Results are mean percentages±SE from 24 individual mice from two independent experiments.

Figure 3A:
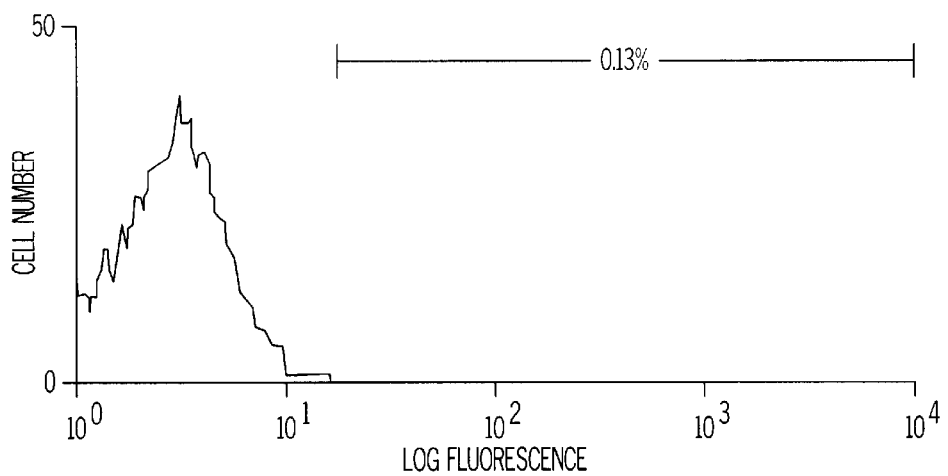
FIGS. 3a–3c FACS analysis of $Thy-1,2^{+T}$ cells within the spleen of a congenic NOD-N Thy-1,1 mouse.
Figure 3B:
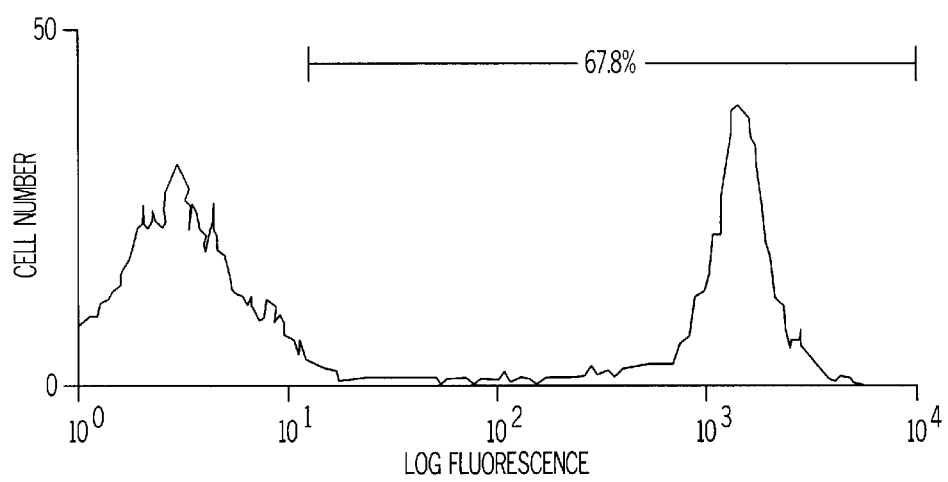
Figure 3C:
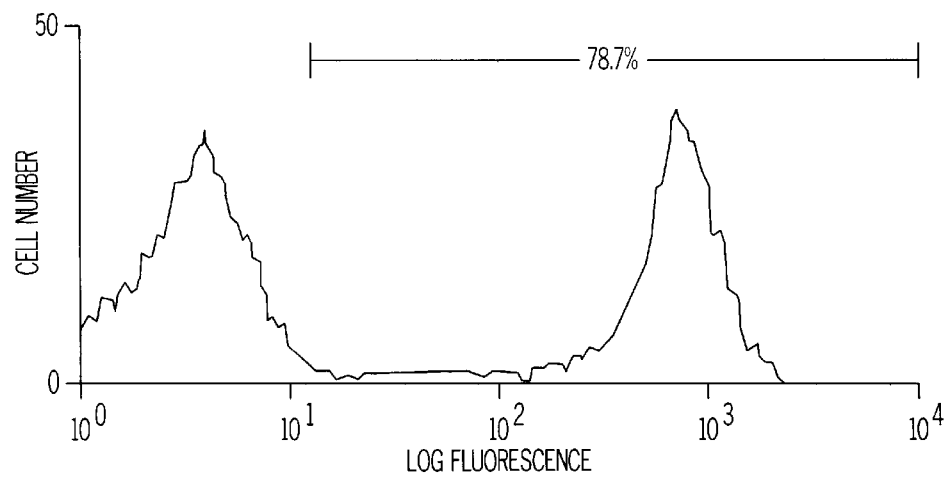
Figure 4A:
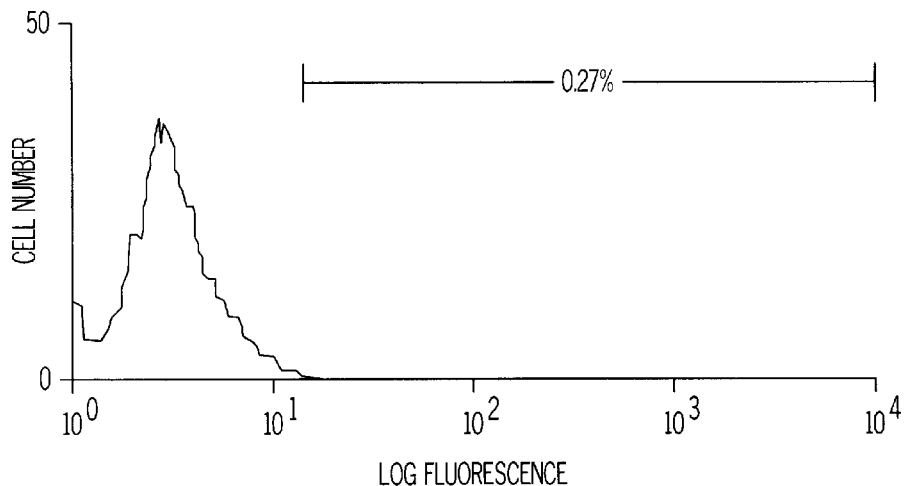
FIGS. 4a–4c FACS analysis of $Thy-1,2^{+T}$ cells within the thymus of a congenic NOD-N Thy-1,1 mouse.
Figure 4B:
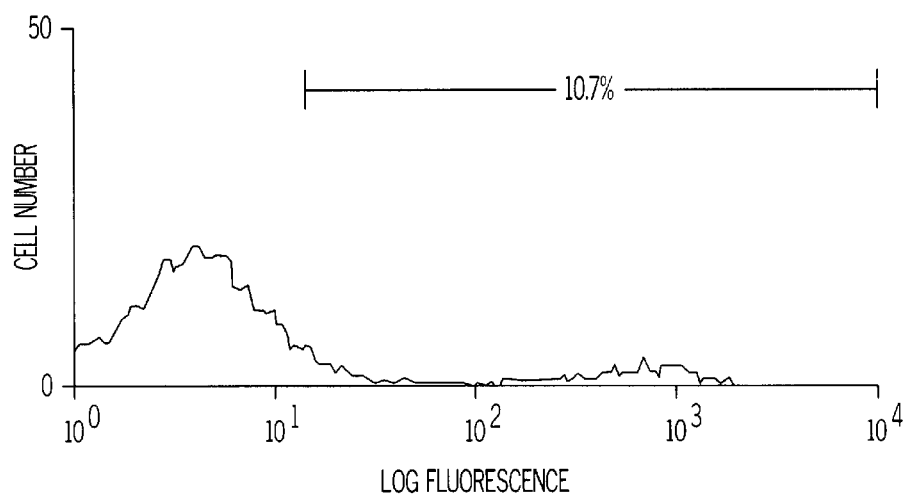
Figure 4C:
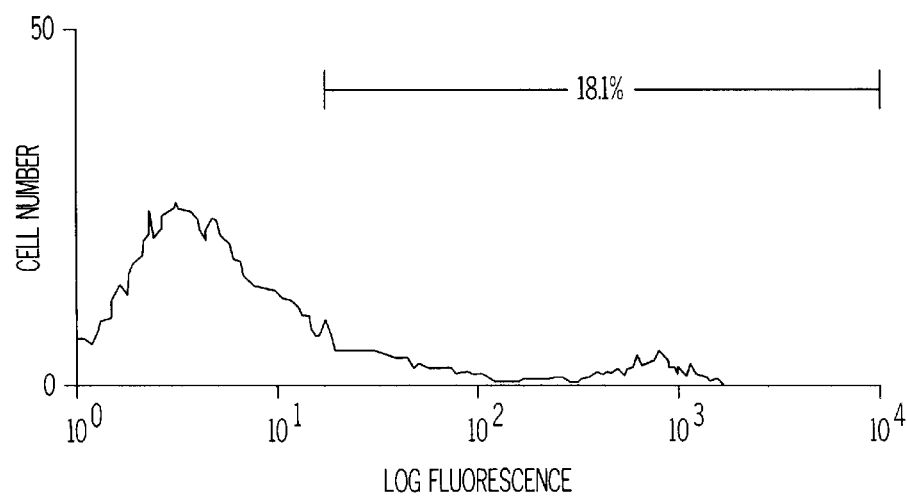

FIGS. 3a, 3b and 3c: FACS analysis of Thy-1,2$^+$ T cells within the spleen of a congenic NOD-N Thy-1,1 mouse, three weeks after sub-lethal irradiation and inoculation of Thy-1,2$^+$ T cells from diabetic donors. FIG. 3a represents the results in a control NOD-N Thy-1,1 mouse. Insulin like growth factor-1 significantly reduced the number of Thy-1,2$^+$ in the spleen (FIG. 3b) in comparison to saline (FIG. 3c).

FIGS. 4a, 4b and 4c: FACS analysis of Thy-1,2$^+$ T cells within the thymus of a congenic NOD-N Thy-1,1 mouse, three weeks after sub-lethal irradiation and inoculation of Thy-1,2$^+$ T cells from diabetic donors. FIG. 4a represents the results in a control NOD-N Thy-1,1 mouse. The effects of rhIGF-1 upon the reconstitution of the thymus after T cell transfer are shown in FIG. 4b and are compared to saline injected mouse (FIG. 4c).

TABLE I

Variation in the body weight of experimental mice injected with IGF-1, insulin or saline over a period of 3 weeks. Each value represents the mean ± SE (n).

| Treatment | Weight (g) Day 1 | Day 21 | p value |
|---|---|---|---|
| Saline | 30.13 ± 0.38 (n = 22) | 28.71 ± 0.49 (n = 21) | 0.027 |
| Insulin | 29.61 ± 0.39 (n = 17) | 28.13 ± 0.44 (n = 14) | 0.018 |
| rhIGF-1 | 29.63 ± 0.34 (n = 24) | 29.68 ± 0.52 (n = 24) | 0.946 |

TABLE II

Flow cytometry analysis of Thy-1,2$^+$, L3T4$^+$ and Lyt-2$^+$ T cells in the spleens of experimental mice treated with rhIGF-1 or saline. Results are mean ± SE of individual analysis performed on 12 different mice from each group.

| Treatment | Percentage of cell population Thy-1,2$^+$ | L3T4$^+$ | Lyt-2$^+$ |
|---|---|---|---|
| Saline | 14.78 ± 1.05 | 14.98 ± 0.76 | 6.63 ± 0.39 |
| rhIGF-1 | 21.95 ± 1.87 | 12.72 ± 1.48 | 5.19 ± 0.62 |
| p value | 0.266 | 0.258 | 0.104 |

TABLE III

Percentages of Thy-1,2$^+$ T cells in the spleen and thymus of experimental congenic NOD-N Thy-1,1 mice three weeks after sub-lethal irradiation and adoptive transfer of 7 × 10$^6$ Thy-1,2$^+$ from diabetic donors. Results are the mean ± SE of 12 individuals mice.

| | Thymocytes n(×10$^6$) | % of Thy-1,2$^+$ T cells | n(×10$^6$) | Splenocytes % of Thy-1,2$^+$ T Cells |
|---|---|---|---|---|
| rhIGF-1 (n = 6) | 36.8 ± 2.3 | 68.43 ± 3.2 | 60 ± 2.4 | 10.86 ± 0.5 |
| saline (n = 6) | 35.1 ± 1.5 | 72.88 ± 2.5 | 56 ± 4.8 | 17.19 ± 1.6 |
| p value | 0.559 | 0.306 | 0.102 | 0.004 |

REFERENCES

1. Castano, L., Eisenbarth, G. S.: Type 1 diabetes: a chronic autoimmune disease of human, mouse and rat. Ann. Rev. Immunol 1990; 8:647–679.
2. Makino, S., Kunimoto, K., Mureoka, Y., Mizushima, Y., Katagiri, X., Tochino, Y.: Breeding of a non-obese diabetic strain of mice. Exp. Anim. 1980;29:1–13.
3. Wicker, L. S., Miller, B. J., Mullen Y.: Transfer of autoimmune diabetes mellitus with splenocytes from non-obese diabetic (NOD) mice. Diabetes 1986;35:855–860.
4. Thivolet, D. H., Bendelac, A., Bedossa, P., Bach, J. F., Camaud, C.: CD8$^+$ T-cell homing to the pancreas in the non-obese diabetic mouse is CD4$^+$ T-cell-dependent. J. Immunol. 1991;146:85–88.
5. Atkinson, M. A., MacLaren, N. K., Luchetta, R.: Insulitis and diabetes in NOD mice reduced by prophylactic insulin therapy. Diabetes 1990;39:933–937.
6. Thivolet, C. H., Goillot, E., Bedossa, P., Durand, A., Bonnard, M., Orgiazzi, J.: Insulin prevents adoptive cell transfer of diabetes in the autoimmune non-obese diabetic mouse. Diabetologia 1991;34:314–319.
7. Like, A. A.: Insulin injections prevent diabetes (DB) in biobreeding/Worcester (BB/Wor) rats. Diabetes 1986;35 (suppl. 1):74.
8. Bertrand, S., De Paepe, M., Vigeant, C., Yale, J. F.: Prevention of adopitve transfer in BB rats by prophylactic insulin treatment. Diabetes 1992;41: 1273–77.
9. Binz, K., Joller,P., Froesch, P., Binz, H., Zapf, J., Froesch, E. R.: Repopulation of the atrophied thymus in diabetic rats by insulin like growth factor 1. Proc. Antl. Acad. Sci. USA 1990;87:3690–3694.
10. Prochazka, M., Serreze, D. V., Worthen, S. M., Leiter, E. H.: Genetic control of diabetogenesis in NOD/Lt Mice: Development and analysis of congenic stocks, Diabetes 1989;38: 1446–1455.
11. Jacob, R. M., Sherwin, R. S., Bowen, L., Fryberg, D., Fagin, K. D., Tamborlane, W. V., Shulman, G. I.: Metabolic effects of IGF-1 and insulin in spontaneously diabetic BB/w rats. Am. J. Physio. 1991;260: E262–E268.
12. Van Schravendijk, C. F. H., Foriers, A., Van den Brande, J. L., Pipeleers, D. G,: Evidence for the presence of Type 1 insulin like growth factor receptors on rat pancreatic A and B cells, Endocrinology 1987;121:1784–1788.
13. Swenne, I., Pancreatic beta-cell growth and diabetes-mellitus. Diabetologia 1992;35: 193–201.
14. Smith, F. E., Rosen K. M., Villa-Komaroff, L., Weir, G. C., Bonner-Weir, S., Enhanced insulin-like growth factor 1 gene expression in regenerating rat pancreas, Proc. Natl. Acad. Aci. USA 1991, 88:6152–6156.
15. Guler, H. P., Schmid, C., Zapf, J., Froesch, E. R.: Effects of recombinant insulin-like growth factor 1 on insulin secretion and renal function in normal human subjects, Proc. Natl. Acad. Sci. USA 1989;86:2868–2872.
16. Hunt, U., Eardley, D. D.: Suppressive effects of insulin and insulin like growth factor 1 (IGF-1) on immune responses. J. Immunol. 1986;136:3994–3999.
17. Baxter, J. B., Blalock, J. E., Weigent, D. A.: Characterization of Immun oreactive Insulin-Like Growth Factor-1 from Leukocytes and Its Regulation by Growth Hormone. Endocrinology 1991;129: 1727–1734.
18. Tapson, V. F., Boni Schnetzler, M., Pilch, P. F., Center, D. M., Berman, J. S.: Structural and functional characterization of the human T-lymphocyte receptor for insulin-like growth-I in vitro. J. Clin. Invest. 1988;82:950–957.
19. Stuart, C. A., Meehan R. T., Neale, L. S., Cintron, N. M., Furlanetto, R. W.: Insulin-like growth factor binds selectively to human peripheral blood monocytes and B-lymphocytes. J. Clin. Endocrinol. Metabol. 1991; 72:1117–1122.
20. Koijman, R., Willems, M., Dehaas, C. J. C., Rijkers, G. T., Schuurmans, A. L. G., Vanbuuloffers, S. C.: Expression of type-1 insulin-like growth factor receptros on human peripheral blood mononuclear cells, Endocrinology 1992; 131: 2244–2250.
21. Timsit, J., Savino, W., Safieh, B., Chanson, P., Gagnerault, M. C., Bach, J. G., Dardenne, M.: Growth hormone and insulin-like factor 1 stimulate hormonal function and proliferation of tyhymic epithelial cells, J. Clin. Endocrinol. Metab. 1992;75: 183–188.
22. Clark, R., Strasse, J., McCabe, S., Rabbins, K., Jardieu, P.: Insulin-like growth factor-1 stimulation of lymphopoiesis, J. Clin. Invest. 1993;92:540–548.
23. Bedossa, P., Bendelac, M., Bach, J. F., Camaud, C., Syngeneic T cell transfer of diabetes into NOD newborn mice: in situ studies of the autoimmune steps leading to insulin producing cell destruction, Eur.J. Immunol. 1989;19:1947–1951.

What is claimed is:

1. Method for delaying the clinical onset of diabetes by administration of IGF-I.

2. A method according to claim 1, wherein the IGF-I is administered in a daily dosage of from 20 to 500 µg/kg.

3. A method according to claim 1 wherein the IGF-I is administered in a daily dosage of from 20 to 250 µg/kg.

4. A method according to claim 1, wherein the IGF-I is administered in a daily dosage of from 100 to 200 µg/kg.

5. Method for reducing the occurrence of beta cell destruction in a subject having a high risk of developing diabetes by administration of IGF-I.

6. A method according to claim 5, wherein the IGF-I is administered in a daily dosage of from 20 to 500 µg/kg.

7. A method according to claim 5, wherein the IGF-I is administered in a daily dosage of from 20 to 250 µg/kg.

8. A method according to claim 5, wherein the IGF-I is administered in a daily dosage of from 100 to 200 µg/kg.

9. Method for reducing the number of T cells migrating to the spleen in a subject having a high risk of developing diabetes by administration of IGF-I.

10. A method according to claim 9, wherein the IGF-I is administered in a daily dosage of from 20 to 500 µg/kg.

11. A method according to claim 9, wherein the IGF-I is administered in a daily dosage of from 20 to 250 µg/kg.

12. A method according to claim 9, wherein the IGF-I is administered in a daily dosage of from 100 to 200 µg/kg.

* * * * *